(12) United States Patent
Song et al.

(10) Patent No.: US 11,393,138 B2
(45) Date of Patent: Jul. 19, 2022

(54) RELAXED ITERATIVE MAXIMUM-LIKELIHOOD EXPECTATION MAXIMIZATION FOR POSITRON EMISSION TOMOGRAPHY RANDOM COINCIDENCE ESTIMATION

(71) Applicant: KONINKLIJKE PHILIPS N.V., Eindhoven (NL)

(72) Inventors: Xiyun Song, Cupertino, CA (US); Jinghan Ye, Livermore, CA (US); Andriy Andreyev, Highland Heights, OH (US); Chuanyong Bai, Solon, OH (US); Zhiqiang Hu, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 16/648,397

(22) PCT Filed: Sep. 20, 2018

(86) PCT No.: PCT/EP2018/075534
§ 371 (c)(1),
(2) Date: Mar. 18, 2020

(87) PCT Pub. No.: WO2019/057851
PCT Pub. Date: Mar. 28, 2019

(65) Prior Publication Data
US 2020/0286266 A1 Sep. 10, 2020

Related U.S. Application Data

(60) Provisional application No. 62/561,235, filed on Sep. 21, 2017.

(51) Int. Cl.
*G06T 11/00* (2006.01)
*A61B 6/03* (2006.01)
(Continued)

(52) U.S. Cl.
CPC .......... *G06T 11/008* (2013.01); *A61B 6/037* (2013.01); *G01T 1/2985* (2013.01);
(Continued)

(58) Field of Classification Search
CPC ............... G06T 1/2985; G06T 7/0012; G06T 11/005; G06T 11/008; G06T 2207/10104; G06T 2207/30004; G06T 2211/424; A61B 6/037
See application file for complete search history.

(56) References Cited

U.S. PATENT DOCUMENTS 8,265,365 B2 9/2012 Panin
10,101,474 B2 * 10/2018 Laurence ................ G01T 1/249
(Continued)

FOREIGN PATENT DOCUMENTS

WO 2016097977 A1 6/2016

OTHER PUBLICATIONS

Byars et al. "Variance reduction on randoms from coincidence histograms for the HRRT." IEEE Nuclear Science Symposium Conference Record, 2005. vol. 5. IEEE, 2005. (Year: 2005).*
(Continued)

*Primary Examiner* — Katrina R Fujita (57) ABSTRACT

A non-transitory storage medium stores instructions readable and executable by an electronic processor (20) to perform a method (100) for estimating singles rates for detectors (16) of a detector array (14) of a positron emission tomography (PET) imaging device (12). The method includes: obtaining measured delayed coincidence rates for lines of response (LORs) defined by pairs of the detectors of the detector array; and generating estimated singles rates for the detectors of the detector array by an iterative optimization in which each iteration performs an update of estimates of the singles rates for the detectors by operations including: forward projecting the estimates of the singles rates for the
(Continued)

detectors to generate estimates of delayed coincidence rates for the LORs; generating quantitative comparisons between the measured delayed coincidence rates for the LORs and the generated estimates of the delayed coincidence rates for the LORs; backprojecting the quantitative comparisons to generate corrections for the singles rates for the detectors; and updating the estimates of the singles rates for the detectors using the generated corrections. The estimated singles rates for the detectors of the detectors array comprise the estimates of the singles rates for the detectors output by the iterative optimization when the iterative optimization satisfies a stopping criterion. This process jointly optimizes the estimated singles rates and randoms estimation.

23 Claims, 5 Drawing Sheets (51) Int. Cl.
G01T 1/29 (2006.01)
G06T 7/00 (2017.01)
(52) U.S. Cl.
CPC .............. G06T 7/0012 (2013.01); G06T 2207/10104 (2013.01); G06T 2207/30004 (2013.01)

(56) References Cited

U.S. PATENT DOCUMENTS

| | | | |
|---|---|---|---|
| 2005/0129170 A1* | 6/2005 | Watson | G01T 7/005 378/5 |
| 2009/0072154 A1* | 3/2009 | Watson | A61B 6/037 250/363.03 |
| 2010/0057819 A1 | 3/2010 | Panin | |
| 2012/0126125 A1* | 5/2012 | Akazawa | A61B 6/037 250/363.04 |
| 2014/0194735 A1* | 7/2014 | Panin | A61B 6/5258 600/425 |
| 2015/0119694 A1* | 4/2015 | Mihlin | G01T 1/2985 600/411 |
| 2015/0213630 A1* | 7/2015 | Szirmay-Kalos | G06T 1/20 382/131 |
| 2016/0174919 A1* | 6/2016 | Ahn | A61B 5/0059 382/131 |
| 2017/0032545 A1 | 2/2017 | Mihlin | |
| 2017/0046857 A1* | 2/2017 | Ye | G06T 11/005 |
| 2017/0091963 A1* | 3/2017 | Panin | A61B 6/037 |
| 2018/0021009 A1* | 1/2018 | Ye | A61B 6/037 250/252.1 |
| 2018/0165839 A1* | 6/2018 | Lv | G06T 7/10 |
| 2019/0287275 A1* | 9/2019 | Zhu | G06T 7/0012 |
| 2019/0361136 A1* | 11/2019 | Song | G01T 7/00 |

OTHER PUBLICATIONS

Vandenberghe et al. "Randoms correction for gamma camera based PET list-mode reconstruction." 2001 IEEE Nuclear Science Symposium Conference Record (Cat. No. 01CH37310). vol. 4. IEEE, 2001. (Year: 2001).*

Knoll, G. F., "Radiation Detection and Measurement"., 3rd Ed. New York, NY: John Wiley & Sons 1999.

Casey, M.E., Hoffman, E.J. "Quantitation in Positron Emission Computed Tomography: 7 A Technique to Reduce Noise in Accidental Coincidence Measurements and Coincidence Efficiency Calibration", J. Comput Assist Tomogr. 1986; 10;845-850.

Stearns, C.W., McDaniel, D.L., Kohlmyer, S.G., Arul, P.R., Geiser B.P., Shanmugam, V. Random Coincidence Estimation From Single Event Rates on Discovery ST PET/CT Scanner. Proceedings of the 2003 IEEE Nuclear Science Sypmposium and Medical Imaging Conference, Portland, OR: IEEE. 2003;5:3067-3069.

International Search Report, dated Dec. 13, 2018.

Christian, W, et al "Time of Flight PET Image Reconstruction Using Origin Ensembles", Phy. in Med. and Biol., 60, 2015, pp. 1919-1944.

Michel, D. et al., "ML Estimation of the Scatter Scaling in TOF PET", 2014. IEEE.

Brasse et al. Correction Methods for Random Coincidences in Fully 3D Whole-Body PET: Impact on Data and Image Qualtiy:, JNM 2005; 46(5);859-867.

* cited by examiner

RELAXED ITERATIVE MAXIMUM-LIKELIHOOD EXPECTATION MAXIMIZATION FOR POSITRON EMISSION TOMOGRAPHY RANDOM COINCIDENCE ESTIMATION

CROSS-REFERENCE TO PRIOR APPLICATIONS

This application is the U.S. National Phase application under 35 U.S.C. § 371 of International Application No. PCT/EP2018/075534, filed on Sep. 20, 2018, which claims the benefit of U.S. Provisional Application No. 62/561,235, filed on Sep. 21, 2017. These applications are hereby incorporated by reference herein.

FIELD

The following relates generally to the medical imaging arts, positron emission tomography (PET) imaging arts, PET image reconstruction and post-reconstruction processing arts, and related arts.

BACKGROUND

High quality and accurate quantitative reconstruction of positron emission tomography (PET) images requires correction for random coincidences ("randoms"). Different methods have been previously proposed for randoms correction. One such method uses a delayed coincidence window to model the randoms recorded in the prompt window, based on the assumption that the number of random coincidences detected as delayed coincidences equals to, on average, the number of random coincidences in the prompt coincidence sinogram (see Noll G. Radiation Detection and Measurement. 3rd ed. New York, N.Y.: John Wiley & Sons; 1999). One drawback of the delayed coincidence methods is statistical noise in the delayed coincidence data. In order to reduce noise, smoothing of the delayed coincidence data or other averaging strategy may be employed, but these approaches can introduce extra bias and/or compromise accuracy.

A Casey averaging step can be employed to smooth the noise (see, Casey M E, Hoffman E J. Quantitation in positron emission computed tomography: 7. A technique to reduce noise in accidental coincidence measurements and coincidence efficiency calibration. J Comput Assist Tomogr. 1986; 10:845850). Problematically, since Casey averaging is applied to the delayed sinogram (rather than the prompt sinogram), the effect of detector geometry response correction applied to both the delayed and prompt sinograms in earlier steps becomes unmatched for the delayed and prompt sinogram. This leads to undesired wave shape in axial profiles from reconstructed images of a uniform cylinder phantom.

Another category of randoms correction methods includes estimating randoms from singles rates, referred to as "singles-based" approach based on the theoretical relationship between singles rates and random coincidence rates. These methods requires singles rate of each detector or each detector block to be available, and requires the singles rates should reflect those single photons that can lead to random coincidences, and typically also requires scaling of estimated randoms to match the amount of the delayed coincidences from acquisition (see, Stearns C W, McDaniel D L, Kohlmyer S G, Arul P R, Geiser B P, Shanmugam V. Random coincidence estimation from single event rates on the Discovery S T PET/CT scanner. Proceedings of the 2003 IEEE Nuclear Science Symposium and Medical Imaging Conference. Portland, Oreg.: IEEE. 2003; 5:3067-3069).

US Pat. Pub. No. 2009/0072154, describes a method of randoms correction using both the delayed coincidences and singles rates to reduce data variance. This method derives an averaged estimate of $R_{ij}$ of the randoms event (delayed) sinogram corresponding to detectors i and j in a detector ring as below:

$$\hat{R}_{i,j} = \frac{R_i R_j}{2\tau(\Sigma_{i' \in J_i} S_{i'})(\Sigma_{j' \in I_j} S_{j'})}$$

where $R_i$ and $R_1$ are the fan sum of the delayed coincidence for detectors i and j; $S_{i'}$, and $S_{j'}$, are the singles rates of the detectors corresponding to the fan of detector i and j, respectively. This approach requires the singles rates to be available, and it either uses approximate solution or still not takes full advantage of all the data available for the estimation, as discussed in the prior art itself.

WO Pub. No. 2016/097977, describes methods "to derive singles rate per detector element from delay rate" and "to establish the relationship of singles rate for each detector element from the random rate for that element". As disclosed in that reference: 1) "Using random events which are readily available for each LOR, the singles events can be estimated with a proper signal decomposition method"; and 2) the system of nonlinear equations $R_{ij}=2\tau S_i * S_j$ can be "resolved using modern global optimization methods" for the unknown singles rate $S_i$ and $S_j$ given the measurements of delayed coincidence $R_{ij}$. The system of nonlinear equations is solved by rebinning delayed coincidence events to 2-D map or histogram that is in effect the singles map with a scaling factor. However, this is a single pass method and the result is an approximate of singles rate map, convergence and accuracy of resolving the nonlinear equations are not guaranteed due to data complexity. Alternative approaches disclosed in that reference include solving "the nonlinear system of equations using a global optimization method such as least squares minimization method or the like." A wide range of least squares minimization methods could be employed, e.g. Stochastic Gradient Descent (SGD), the Levenberg-Marquardt algorithm, or so forth. Least squares minimization techniques have some advantages, but can be sensitive to the initial values of the unknowns (here the singles rates) and can be difficult to tune performance.

The following discloses new and improved systems and methods to overcome these problems.

SUMMARY

In one disclosed aspect, a non-transitory storage medium stores instructions readable and executable by an electronic processor to perform a method for estimating singles rates for detectors of a detector array of a positron emission tomography (PET) imaging device. The method includes: obtaining measured delayed coincidence rates for lines of response (LORs) defined by pairs of the detectors of the detector array; and generating estimated singles rates for the detectors of the detector array by an iterative optimization in which each iteration performs an update of estimates of the singles rates for the detectors by operations including: forward projecting the estimates of the singles rates for the detectors to generate estimates of delayed coincidence rates for the LORs; generating quantitative comparisons between the measured delayed coincidence rates for the LORs and the generated estimates of the delayed coincidence rates for the LORs; backprojecting the quantitative comparisons to generate corrections for the singles rates for the detectors; and updating the estimates of the singles rates for the detectors using the generated corrections. The estimated singles rates for the detectors of the detectors array comprise the estimates of the singles rates for the detectors output by the iterative optimization when the iterative optimization satisfies a stopping criterion. Estimates for the low-noise random coincidences are generated from the estimated singles rates.

In another disclosed aspect, an imaging system includes a positron emission tomography (PET) imaging device with a detector array having detectors. At least one electronic processor is programmed to: obtain measured delayed coincidence rates for lines of response (LORs) defined by pairs of the detectors of the detector array; and generate estimated singles rates for the detectors of the detector array by an iterative optimization including one of a maximum-likelihood-expectation maximization (ML-EM) and an ordered subset expectation maximization (OSEM) in which each iteration performs an update of estimates of the singles rates for the detectors.

In another disclosed aspect, an imaging system includes a positron emission tomography (PET) imaging device with a detector array having detectors. At least one electronic processor is programmed to: obtain measured delayed coincidence rates for lines of response (LORs) defined by pairs of the detectors of the detector array; and generate estimated singles rates for the detectors of the detector array by an iterative forward projection/backprojection algorithm in which each iteration performs an update of estimates of the singles rates for the detectors.

One advantage resides in deriving random coincidence rates for lines of response with reduced noise or bias due to smoothing.

Another advantage resides in providing single coincidence rates for lines of responses of a positron emission tomography (PET) imaging device.

Another advantage resides in calibrating an image acquisition device to eliminate bias between random rates and singles rates.

Another advantage resides in improved accuracy in random coincidence rates.

Another advantage resides in improved result of singles rates estimates.

Another advantage resides in matching derived singles rates to a total singles rate and matching the estimate of random rates to the amount of delayed coincidences from measurements.

Another advantage resides in providing one or more of the foregoing benefits with improved computational efficiency by leveraging existing iterative forward projection/backward projection optimization architecture typically employed in PET image reconstruction.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

The following proposes an improved computation of random coincidence rates for lines of response (LORs). The rate of "delayed" coincidences is measured along each LOR(i,j) where i and j are detectors defining LOR(i,j). This dataset is very sparse, i.e. for reasonable data collection times many LORs have no counts and those with counts are low, e.g. the total counts for the LOR(i,j) may be only 1, or 2, or 3, or so. To address the data sparsity, in one conventional approach the resulting sinogram is resampled to generate a "small" sinogram of coarser resolution. This small sinogram is still noisy, and this is addressed by performing smoothing, e.g. Casey averaging.

A problem with this approach is that the smoothing, by operating in sinogram space, produces artifacts or errors into the random coincidence rates.

In the disclosed approach, the delayed randoms are used to estimate the singles rates for the detectors. In WO Pub. No. 2016/097977 this is done by solving a system of equations using a histogram or rebinning approach, or using least squares optimization. By contrast, in some illustrative embodiments disclosed herein, a maximum likelihood-expectation maximization (ML-EM) method is applied to estimate the singles rates. Analogizing to ML-EM image reconstruction, current estimates of the singles rates are forward-projected into delayed coincidences space, and differences between the forward projections and actually measured delayed coincidence rates are back projected to generate adjustments to the singles rates. The iterative process continues until a stopping criterion is met.

In some embodiments, singles rates of each detector/pixel are derived with high accuracy and robustness from delayed coincidences. The random rate of each detector/pixel are then derived with no need of scaling or calibration for other singles-based methods. To do so, the following systems and methods use the ML-EM algorithm, or another iterative forward/back projection method such as ordered subsets expectation maximization (OSEM), to search for optimal solution of singles rates or effective singles rate distribution. The iterative use of this algorithm achieves better convergence compared with some other techniques such as least squares minimization. A relaxation damping factor optionally controls convergence speed and noise level. It is also contemplated to incorporate prior information, if available, into the iterative forward/back projection update step. In addition, quantitative self-consistence is maintained between the raw delayed coincidence and the output random estimates without involving calibration or scaling between them.

Figure 1:
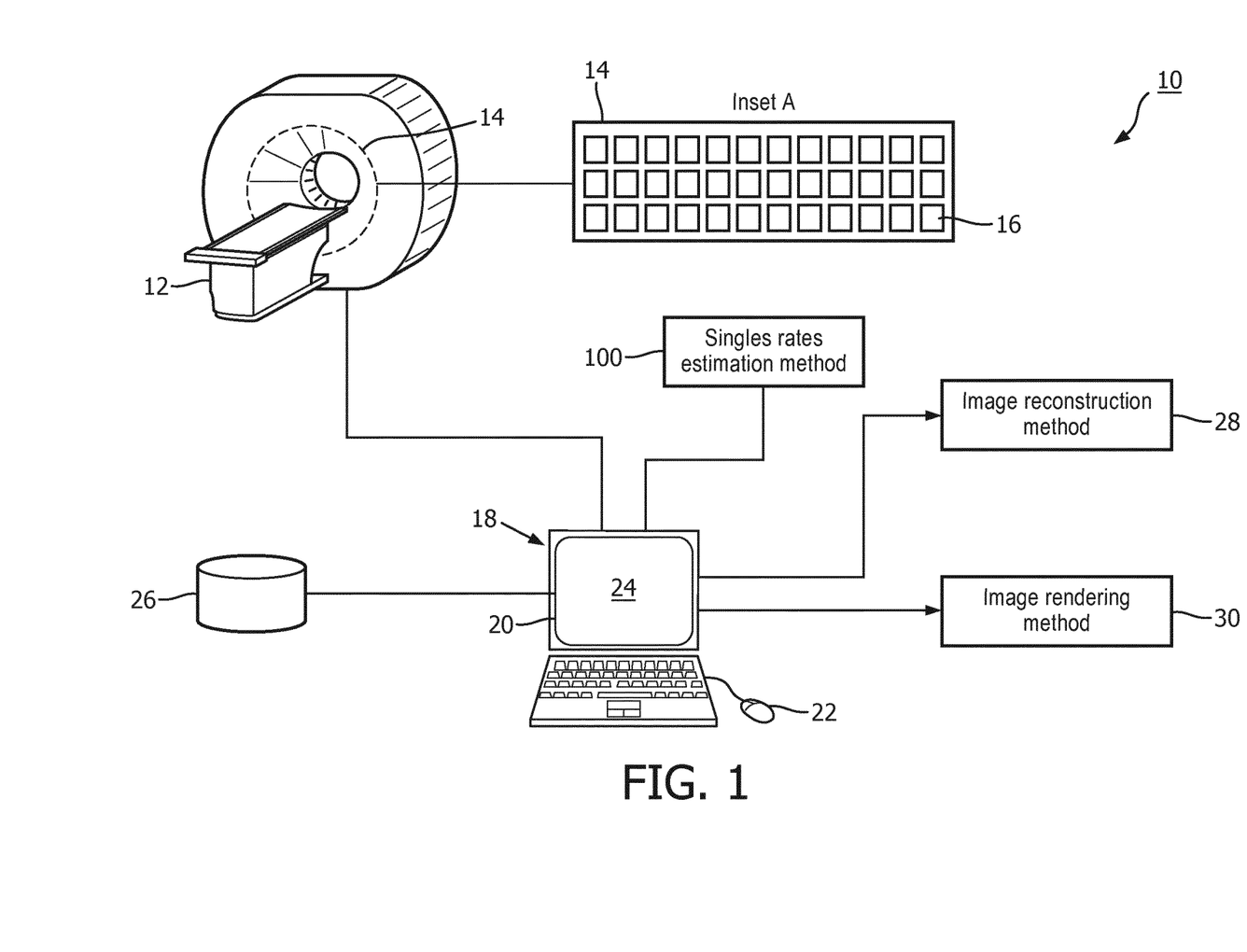
FIG. 1 diagrammatically shows a positron emission tomography (PET) imaging system configured to employ PET detector singles and/or coincidences rate estimation as disclosed herein.

With reference to FIG. 1, an illustrative medical imaging system 10 is shown. As shown in FIG. 1, the system 10 includes a positron emission tomography (PET) imaging device 12. The PET image acquisition device 12 includes a pixelated detector 14 having a plurality of detectors or detector pixels 16 (shown as Inset A in FIG. 1) arranged to collect imaging data from a patient disposed in an examination region. The pixelated detector 14 can, for example, be a detector ring of the PET device 12 (e.g., an entire PET detector ring or a portion thereof, such as a detector tile, a detector module, and so forth).

Optionally, the PET imaging device 12 may have time-of-flight (TOF) localization capability. The PET imaging device 12 detects events (i.e., counts), in which each event comprises two 511 keV gamma ray detection events occurring with a coincidence time window that is narrow enough so that the two events are reasonably assumed to have originated from a single electron-positron annihilation event. It is still possible that randomly two 511 keV gammas each belonging to a different electron-positron annihilation can also be detected in coincidence (i.e., random coincidence event). Each count has an associated line of response (LOR) connecting the two detectors that detected the 511 keV events. Energy windowing about the 511 keV energy may be employed to exclude radiation detection events in which the detected particle has energy well away from 511 keV. If the PET imaging device 12 has time-of-flight (TOF) localization capability, then the time difference between the two 511 keV detection events is used to further localize the event along the LOR, e.g. assigning a Gaussian or other peaked distribution centered at the most likely position based on the time difference (if any) between the two detected events and having a width corresponding to the temporal resolution of the PET detectors.

The system 10 also includes a computer or workstation or other electronic data processing device 18 with typical components, such as at least one electronic processor 20, at least one user input device (e.g., a mouse, a keyboard, a trackball, and/or the like) 22, and a display device 24. In some embodiments, the display device 24 can be a separate component from the computer 18. The workstation 18 can also include one or more databases 26 (stored in a non-transitory storage medium such as a magnetic disk, RAID array, solid state drive, or so forth).

The electronic processor 20 is operatively connected with a non-transitory storage medium (not shown) that stores instructions which are readable and executable by the electronic processor 20 to perform disclosed operations including performing an image reconstruction method 28, performing an image rendering method 30, and performing a method or process 100 for estimating singles rates for the detectors 16 of the detector array 14 of the PET imaging device 12.

The image reconstruction method 28 employs an image reconstruction algorithm to reconstruct events data into a PET image. In some illustrative embodiments, the image reconstruction employs an iterative forward/back projection algorithm such as maximum-likelihood-expectation maximization (ML-EM) and an ordered subset expectation maximization (OSEM). In such an algorithm, estimated pixel intensities of the current image estimate are forward projected into projection space. Quantitative comparisons between the measured projections (that is, the acquired event pairs with corresponding LORs) and the forward projections of the current pixel intensities are generated. These comparisons are back projected to generate corrections for the image pixel intensities, and the pixel intensity estimates are adjusted using these corrections. The process is repeated iteratively so as to bring the forward projection of the image estimate progressively closer to the measured projection data, until some stopping criterion is met. The reconstructed image is then the image estimate at the time the iterating is stopped. The iterative update step may optionally take into account factors such as attenuation using an attenuation map generated from a computed tomography (CT) image of the subject, and/or introduce prior information such as by an edge-preserving prior.

The image rendering method 30 produces a displayable representation of the reconstructed image, e.g. as a three-dimensional (3D) rendering or maximum intensity projection (MIP) of the reconstructed image, or by displaying one or more two-dimensional (2D) slices extracted from the reconstructed image, or so forth. Optionally, the rendering may include advanced features such as performing post-reconstruction image filtering or the like, image fusion to combine the PET image with a corresponding CT image, and/or so forth. The displayable representation is suitably displayed on the display device 24.

In the following, some illustrative embodiments of the method or process 100 for estimating singles rates for the detectors 16 of the detector array 14 are described. As used herein, the term "rate" refers to either the rate (e.g. $r_{ij}=2\tau s_i s_j$, where $r_{ij}$ is a delayed coincidence rate, ij specifies the line of response (LOR) connecting detector elements i and j, and $s_i$ and $s_j$ are singles rate for detectors i and j, and $\tau$ is the coincidence time window width) or the count (e.g., $R_{ij}=2T\tau s_i s_j$, where $R_{ij}$ is the delayed coincidence count for a detector i and any other detector j that form a line of response (LOR) with the detector i. The delayed count quantity $R_{ij}$ is the rate measured for a time interval corresponding to an acquisition time interval T, e.g. if the acquisition time is five minutes then $R_{ij}$ can be understood as the count rate per five minute interval. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the singles rate estimation method or process 100 may be performed by cloud processing.

Figure 2:
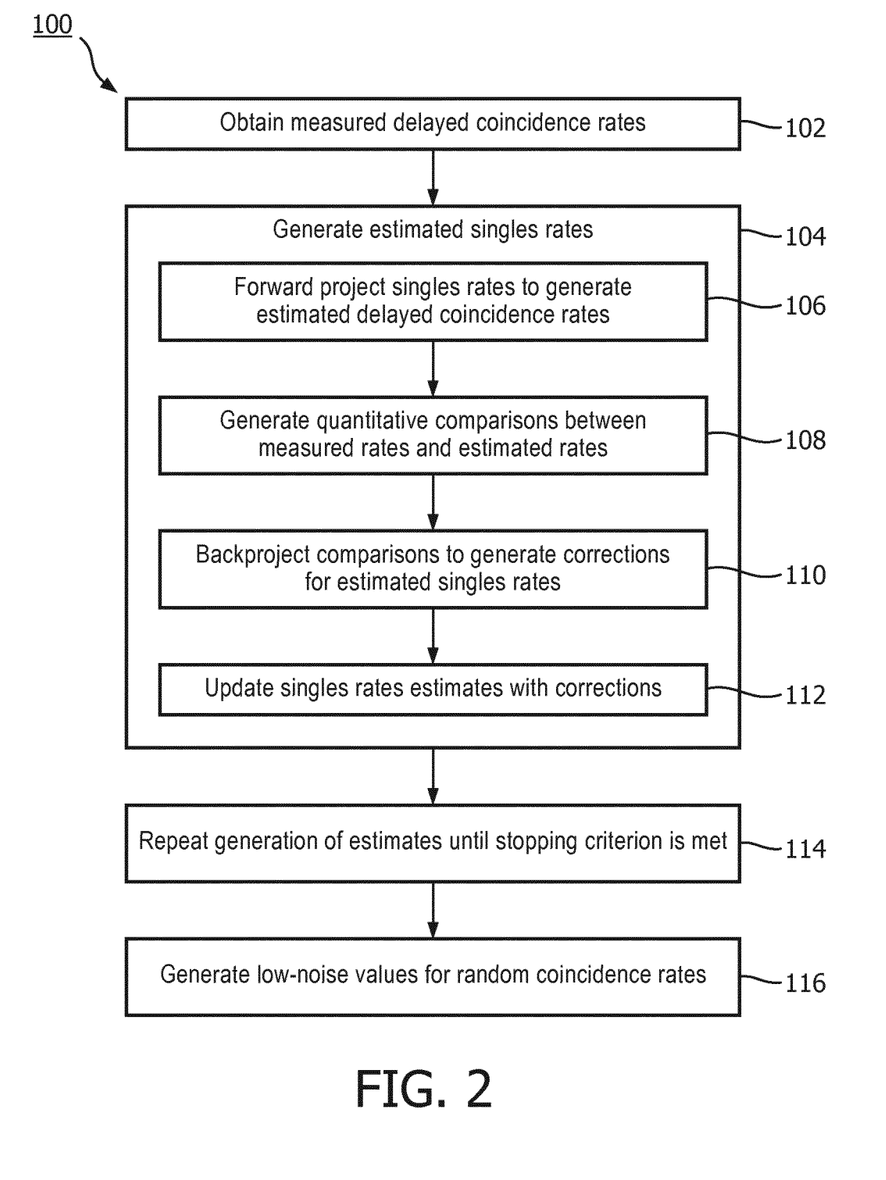
FIG. 2 shows exemplary flow chart operations of an embodiment of the singles rate measurement method performed by the electronic processor of FIG. 1.

With reference to FIG. 2, the singles rate estimation method 100 is diagrammatically shown as a flowchart. At 102, the workstation 18 is configured to obtain or receive measured delayed coincidence rates for lines of response (LORs) defined by pairs of the detectors 16 of the detector array 14. The delayed coincidences are suitably defined by using a delayed coincidence time window of the same width as that used to measure true (i.e. prompt) coincidences, but with a time offset large enough to ensure that the two 511 keV gamma rays are not attributable to the same electron-positron annihilation event. Since they are not due to the same annihilation event, each occurrence is a random event. In this approach, the randoms generation is assumed to be a stationary process, in which case the time offset chosen for measuring the delayed coincidences is arbitrary so long as it is large enough to exclude true coincidences.

At 104, estimated singles rates for the detectors 16 of the detector array 14 are generated by an iterative optimization in which each iteration performs an update of estimates of the singles rates for the detectors. The iterative optimization is an iterative forward/back projection optimization, such as one of a maximum-likelihood-expectation maximization (ML-EM) and an ordered subset expectation maximization (OSEM). The iterative forward/back projection optimization 104 is described in more detail below.

To generate the estimated singles rates, the at least one electronic processor 20 is programmed to perform multiple operations 106-114. At 106, estimates of the singles rates for the detectors 16 are forward projected to generate estimates of delayed coincidence rates for the received LORs. In some examples, the forward projecting includes performing multiplication of corresponding singles $s_i$, and $s_j$ for a LOR between detectors i and j where $s_i$ is the estimate of the singles rate for detector i and $s_s$ is the estimate of the singles rate for detector j.

At 108, quantitative comparisons are generated between the measured delayed coincidence rates for the LORs (acquired at 102) and the generated estimates of the delayed coincidence rates for the LORs (acquired at 106). In some embodiments, the quantitative comparisons are ratios of the measured delayed coincidence rates and the generated estimates of the delayed coincidence rates for the LORs. For example, the quantitative comparison for the LOR between detectors i and j comprises the ratio $$\frac{r_{ij}}{2\tau s_i s_j}$$

or equivalently $$\frac{R_{ij}}{s_i'^{(n)} s_j'^{(n)}}$$

where $r_{ij}$ is the measured delayed coincidence rate for the LOR between detectors i and j. To simplify, the effective singles rates and $s'_i$ and $s'_j$ are defined as $s'_i = \sqrt{2T\tau} s_i$ and $s'_j = \sqrt{2T\tau} s_j$, respectively, which are a constant scaling of $\sqrt{2T\tau}$ from $s_i$ and $s_j$, for all detectors i and j.

At 110, the quantitative comparisons are back projected to generate corrections for the singles rates for the detectors. For detector i, the backprojecting includes a normalization by a sum over all estimated delayed count rates in valid LORs formed by detector i and any other detector j.

At 112, the estimates of the singles rates for the detectors are updated using the generated corrections. In some embodiments, the updating operation includes normalizing the corrections. In other embodiments, the updating operation includes adjusting or computing the estimates or corrections by one or more mathematical relationships. For example, the updating includes adjusting the corrections by a relaxation term $(1-\lambda)+\lambda c$ where c is the correction and $\lambda$ is a relaxation factor. In another example, the update of the estimate of the singles rate for the detector i comprises computing a value based on at least an estimate of the singles rate for detector i; the set of detectors j that can form a valid LOR with the detector i; a measured delayed coincidence rate for the LOR between detectors i and j; an estimate of the singles rate for the other detectors j; and a relaxation factor between 0 and 1. In a further example, the update of the estimate of the singles rate for the detector i comprises computing a value based on at least an estimate of the singles rate for detector i; list mode data of all events that are recorded at an LOR connecting to detector i; the set of detectors j that can form a valid LOR with the detector i; an estimate of the singles rate for the other detectors j; and a relaxation factor between 0 and 1.

At 114, the estimated singles rates for the detectors of the detectors array comprise the estimates of the singles rates for the detectors output by the iterative optimization when the iterative optimization satisfies a stopping criterion. In other words, the at least one electronic processor 20 is programmed to iteratively generate the estimated singles rates for the detectors 16 of the detector array 14 until a stopping criterion is met. The stopping criterion is defined at least a quality index; a number of all detectors in the detector array; an effective singles rate for a selected detector in an imaging data acquisition device; an effective singles rate all other detectors in the detector array; and a delayed coincidence count for the LOR between detectors i and j.

At 116, the at least one electronic processor 20 is programmed to generate smoothed or low-noise values for the random coincidence rates or counts. The smoothed or low-noise values can be generated from at least an expected random count at a $LOR_{ij}$ between detectors i and j; an effective singles rate for a selected detector i; and is an effective singles rate all other detectors j.

Figure 3:
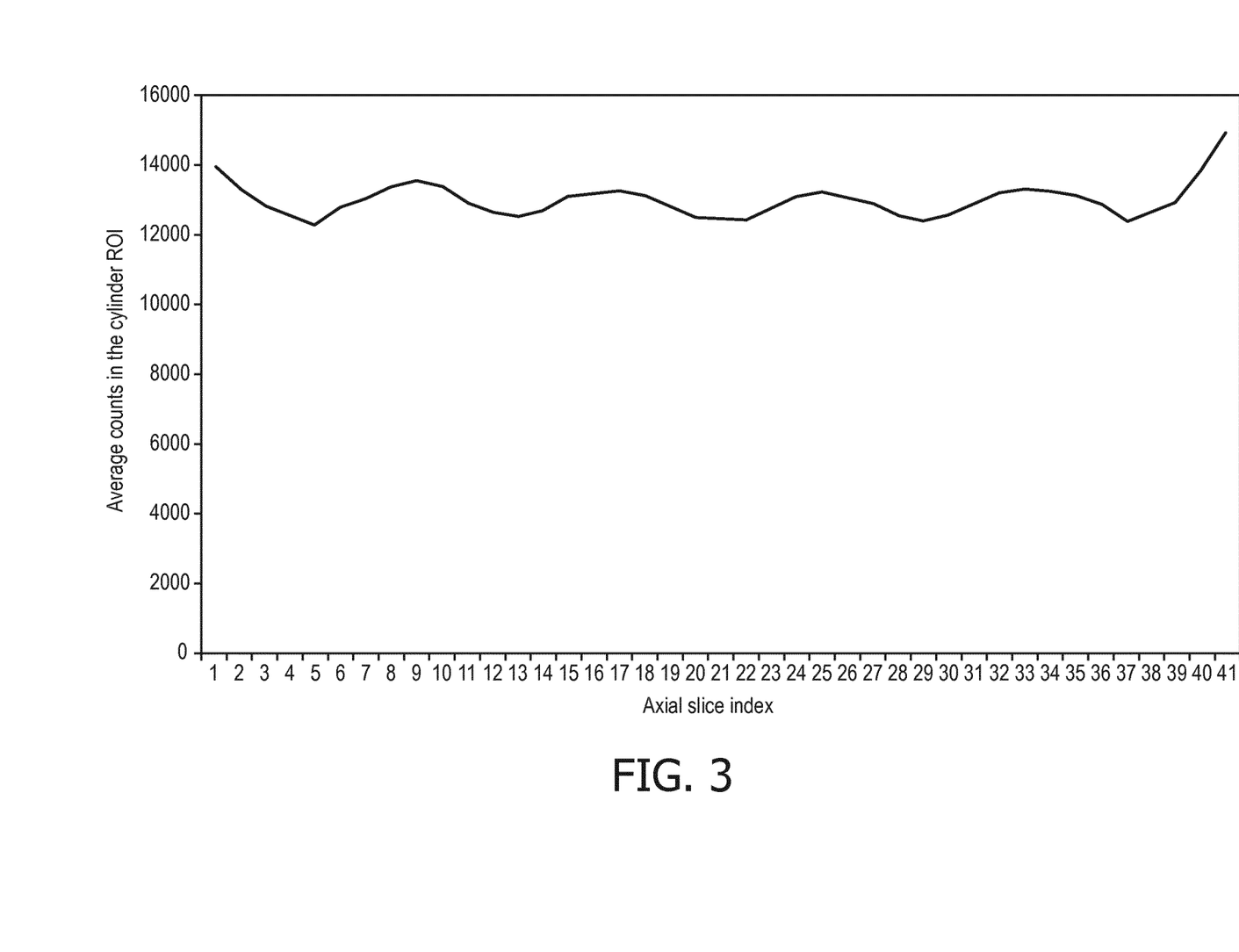
FIGS. 3 and 4 illustratively show an axial profile of a uniform cylinder phantom image reconstructed with Casey smoothing of the delayed sinogram only but without smoothing of the prompt sinogram versus the same axial profile reconstructed corrected using the randoms estimation disclosed herein. 1.
Figure 4:
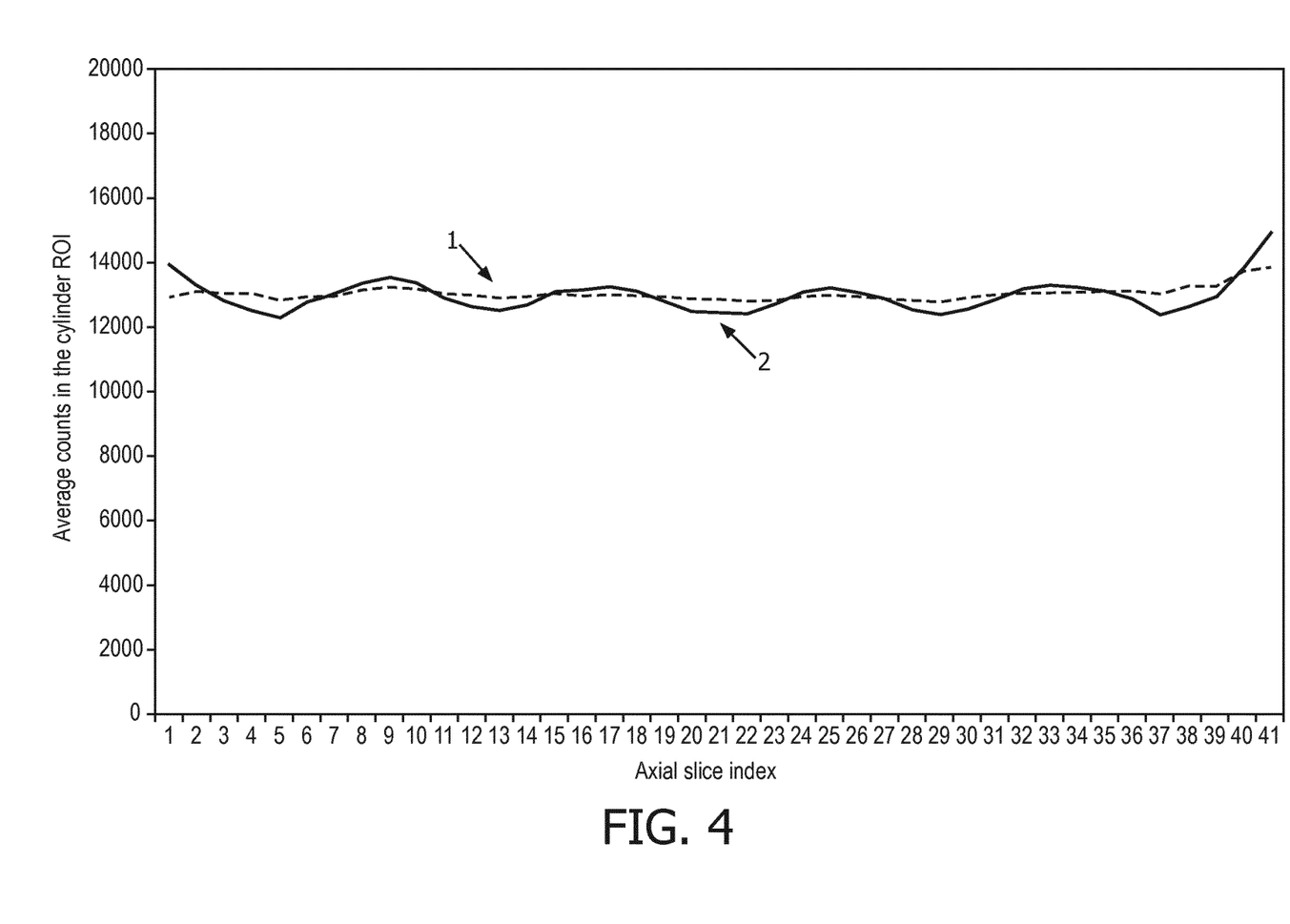

FIGS. 3 and 4 show a comparison between the existing methods and the proposed method. As shown in FIG. 3, a wavy axial profile of a uniform cylinder phantom image reconstructed with Casey smoothing of the delayed sinogram only, but without smoothing of the prompt sinogram. The profile should be a horizontal line, but the discrepancy caused by the unmatched smoothing resulted in the wavy shape artefact. FIG. 4 shows that, using the singles rate estimation method 100, a desired horizontal profile 1 is generated. In FIG. 4, the horizontal profile 1 is superimposed on a wavy profile 2 (per FIG. 3) for clarity.

EXAMPLE

The method 100 starts with raw data of delayed coincidences. The data could be list mode or sinogram format. This example uses a sinogram signal. The data acquisition duration is defined as T, the delayed coincidence count and rate are defined as $R_{ij}$ and $r_{ij}$ respectively, where ij specifies the line of response (LOR) connecting detector elements i and j. Thus, $R_{ij}=r_{ij}\cdot T$. The unknown singles rate are $s_i$ and $s_j$ for detectors i and j, respectively. The established theoretical relationship between the delayed coincidence rate and singles rates is given by Equation 1:

$$r_{ij}=2\tau s_i s_j \quad \text{(Equation 1)}$$

where T is the coincidence time window width. In addition, Equation 2 shows that:

$$R_{ij}=2T\tau s_i s_j \quad \text{(Equation 2)}$$

where $R_{ij}$, T and $\tau$ are the known, and the singles rates of individual detector $s_i$ are the unknowns to solve. Once all $s_i$ unknowns are solved, the expected randoms $\langle R_{ij}\rangle$ can be obtained using Equation (2), which best matches the input R for all ij. Equation (2) represents a system of non-linear equations for all valid i and j.

First, to simplify the problem, the effective singles rates are defined as $s'_i=\sqrt{2T\tau}s_i$, which is a constant scaling of $\sqrt{2T\tau}$ from $s_i$, for all detectors. Then, Equation (2) becomes $$R_{ij}=s'_i s'_j \quad \text{(Equation 3)}$$

Instead of using an approximation method, such as the existing single pass method, Equation 3 is solved as solve it using relaxed ML-EM method as shown in Equation 4:

$$s_i'^{(n+1)} = s_i'^{(n)} \left\{ (1-\lambda) + \lambda \frac{\sum_{j \in \{j_i\}} s_j'^{(n)} \frac{R_{ij}}{s_i'^{(n)} s_j'^{(n)}}}{\sum_{j \in \{j_i\}} s_j'^{(n)}} \right\}, \quad \text{(Equation 4)}$$

for all valid $i$

Figure 5:
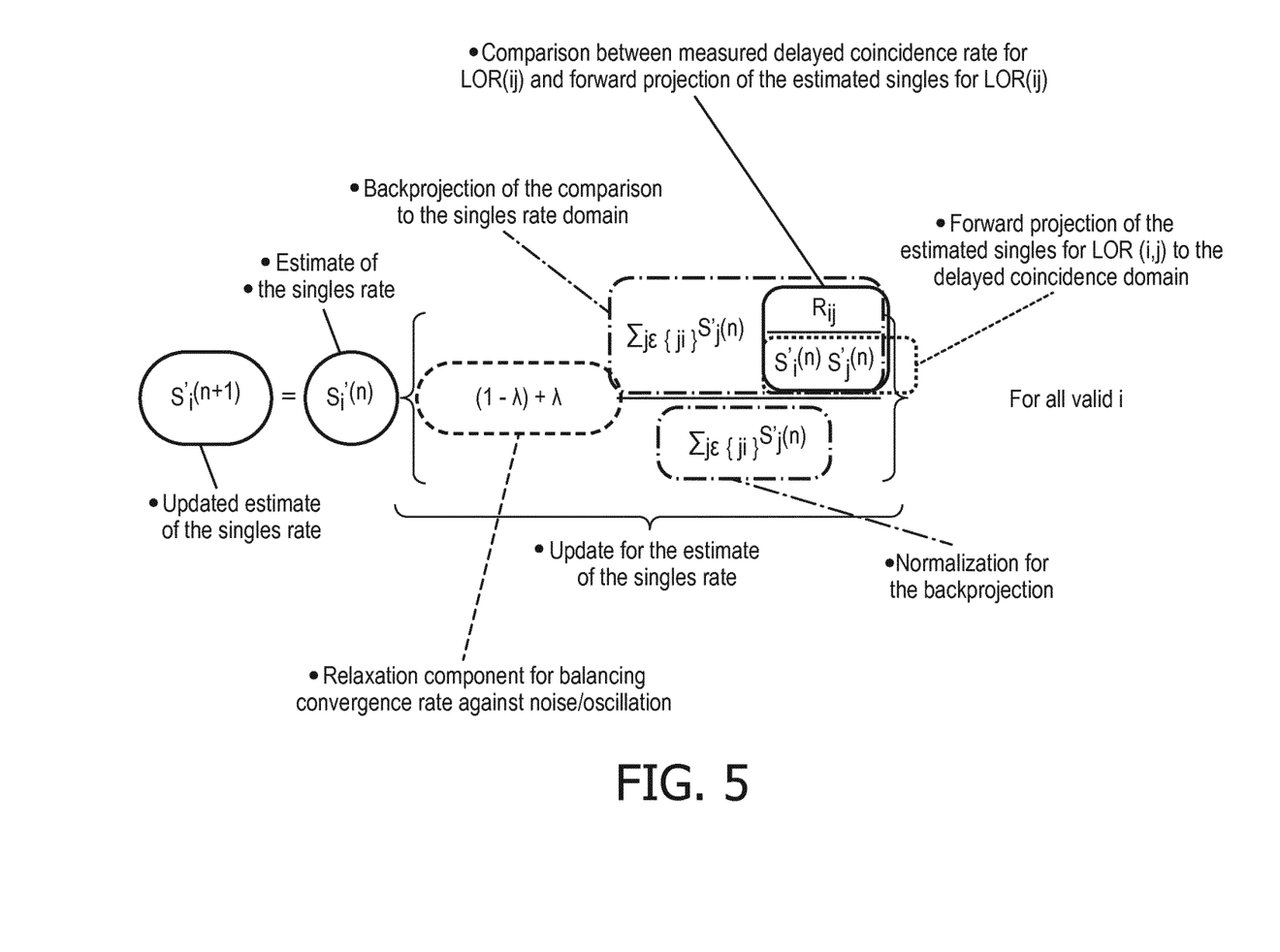
FIG. 5 shows a mapping of process operations to a representative equation for estimating the singles rates for the PET detectors as per the method of FIG. 2.

As shown in FIG. 5, $\{j_i\}$ represents a collection of all other detectors j that can form a valid LOR with detector i. The labels (n) and (n+1) represent the numbers of the previous and the current iteration, respectively. The term $s_i'^{(n)} s_j'^{(n)}$ represents forward-projection from the estimate of the effective singles rates to the delayed coincidence domain.

The ratio of $$\frac{R_{ij}}{s_i'^{(n)} s_j'^{(n)}}$$

represents comparison between the counts of actually measured delayed coincidences and the estimation from forward-projection for the LOR ij. If the ratio is greater than 1, it indicates underestimation of $s'_i$ and/or $s'_j$ in the previous iteration. If the ratio is smaller than 1, then the opposite is true.

$$\sum_{j \in \{j_i\}} s_j'^{(n)} \frac{R_{ij}}{s_i'^{(n)} s_j'^{(n)}}$$

represents backprojection of the ratio to the effective singles rate domain with a weight coming from previous $s'_j$ for update of $s'_i$. $s_j'^{(n)}$ shows up in both the denominator of the ratio term and the back-projector. $\sum_{j \in \{j_i\}} s_j'^{(n)}$ in the denominator represents normalization for the backprojection step. is a relaxation factor between 0 and 1 to control convergence and noise and prevent oscillation. With a larger $\lambda$ (close to 1), the new estimate of $s_i'^{(n+1)}$ takes less weight from the previous estimate $s_i'^{(n)}$, and more weight from the backprojection, thus, convergence should be faster, but with a risk of higher noise and oscillation. In practice, 0.5 can be a good choice for $\lambda$.

Because of the non-linearity of these equations, the backprojection step and calculation of the normalization involve use of $s_j'^{(n)}$ from previous iteration. This is different from conventional ML-EM method for SPECT and PET reconstruction. A variation of Equation (4) is to make all backprojection with equal weights by replacing the $s_j'^{(n)}$ in the backprojection step with unit value to produce Equation 5:

$$s_i'^{(n+1)} = s_i'^{(n)} \left\{ (1-\lambda) + \lambda \frac{\sum_{j \in \{j_i\}} \frac{R_{ij}}{s_i'^{(n)} s_j'^{(n)}}}{\sum_{j \in \{j_i\}} 1} \right\}, \quad \text{(Equation 5)}$$

for all valid $i$

Equations 4 and 5 are for sinogram inputs. Another variation is for delayed coincidences in list mode format, as shown in Equation 6:

$$s_i'^{(n+1)} = s_i'^{(n)} \left\{ (1-\lambda) + \lambda \frac{\sum_{e \in \{e_i\}} s_{j_e}'^{(n)} \frac{1}{s_i'^{(n)} s_{j_e}'^{(n)}}}{\sum_{j \in \{j_i\}} s_j'^{(n)}} \right\}, \quad \text{(Equation 6)}$$

for all valid $i$ where e represents list mode event. $\{e_i\}$ represents the collection of all events that are recorded at an LOR connecting to detector i. $j_e$ represents the other detector for this event. The normalization in the denominator keeps the same as Equation 4 with backprojection of all j that can form a valid LOR with detector i. Fundamentally, Equation 6 and Equation 4 are equivalent. These variations are for the convenience of different input data types, either list mode or sinogram.

The method 100 starts with an initial uniform estimate of the effective singles rates of all detectors. The initial estimate can be set to an average effective singles rate $$s_i'^{(0)} = \frac{\sqrt{2T\tau} \cdot s_{total}}{M},$$

where M is the number of all crystals and $s_{total}$ is the total singles rate of the whole detector system, if it is available from acquisition. However, this is not necessary if random estimation are needed, but not the absolute singles rate map. In fact, the effective singles rate is just an intermediate bridge to connect from delayed coincidences to random coincidences in this method. It can be set to any positive value as long as uniform for all detectors. For example, it can be set to $$\frac{\Sigma R_{ij}}{M}.$$

Thus, the whole process is independent of the knowledge of the total or any singles rate.

The iteration processes to update the new estimates of $s'_i$ to keep looping until certain stopping criteria is met. For example, it can stop after a pre-set maximum number of iterations is reached. It can also stop if the change between iterations is smaller than a pre-set threshold value. For the latter case, a quality index uses the sum of squared error Q, as defined in Equation 7:

$$Q = \sum_{i=1}^{M} \sum_{j \in \{j_i\}} (s_i'^{(n)} s_j'^{(n)} - R_{ij})^2 \quad \text{(Equation 7)}$$

In this scenario, Q is evaluated at the end of each iteration. If the decrease in Q is smaller than the threshold, iterations stop.

In some examples, the iterative optimization algorithm can be an iterative least squares minimization optimization algorithm. The least squared approach minimizes the summed square difference as described in Equation (7). For example, if $$\frac{\partial Q}{\partial s'_i} = \sum_{j \in \{j_i\}} 2(s'_i s'_j - R_{ij}) s'_j = s_{i'} \sum_{j \in \{j_i\}} (s'_j)^2 - \sum_{j \in \{j_i\}} s'_j R_{ij} = 0$$

-continued then $$s'_i = \frac{\sum_{j\in\{j_i\}} s'_j R_{ij}}{\sum_{j\in\{j_i\}} (s'_j)^2}$$

and a possible iterative least squares minimization optimization algorithm is defined in Equation 8:

$$s'^{(n+1)}_i = (s'^{(n)}_i)^{1-\lambda}\left[\frac{\sum_{j\in\{j_i\}}(s'^{(n)}_j R_{ij})}{\sum_{j\in\{j_i\}}(s'^{(n)}_j)^2}\right]^\lambda \quad \text{(Equation 8)}$$

At this point, the effective singles rate map has been generated from the delayed coincidences. This effective singles rate map has a same distribution as the absolute singles rate map, but with a constant scaling factor of $\sqrt{2T\tau}$. For generation of randoms only, there is no need to scaling the effective singles rate map. If the absolute singles rate map need to be saved for other purposes, it can be converted from the effective singles rate map multiplied by $\sqrt{2T\tau}$.

Randoms are estimated for all LORs using Equation 9 or Equation 10:

$$\langle R_{ij}\rangle = s'^{(final)}_i s'^{(final)}_j \quad \text{(Equation 9)}$$

$$\langle R_{ij}\rangle = 2T\tau s_i^{(final)} s_j^{(final)} \quad \text{(Equation 10)}$$

where $\langle R_{ij}\rangle$ represents the expected random count at the $LOR_{ij}$ for this data acquisition with maximum likelihood. Again, no scaling is needed for calculating $\langle R_{ij}\rangle$.

Typically, there is no need to apply smoothing on the result of random estimation. In the case of low count study, the original delayed coincidence data can be very noisy, then filtering or smoothing can be applied to either $s_i^{(final)}$ or the $\langle R_{ij}\rangle$ to control the noise. Again, in this situation, the conventional "smoothed-delayed" approach suffers more than the proposed method 100. Advantageously, the use of iterative updates with ML-EM algorithms to derive the typically unavailable effective singles rates from the commonly available delayed coincidence data, and from there to estimate random component for random correction, with guaranteed convergence from ML-EM algorithm, low noise, high accuracy and robustness.

An advantage of the disclosed approach for estimating the singles rates from the measured delayed coincidence rates is that it employs an iterative forward/back projection algorithm. This type of optimization algorithm is also employed by the image reconstruction method 28. In view of this, the at least one processor 20 is already designed to efficiently perform the iterative forward/back projection algorithm. In some embodiments, the iterative forward/back projection algorithm may be a callable function, module, or the like, which is invoked with suitable inputs by both the image reconstruction method 28 and the method 100 for estimating singles rates. Thus, the disclosed method 100 can reduce memory requirements and increase computational efficiency by leveraging the existing iterative forward/back projection function or method to also perform the singles rate estimation method 100.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A non-transitory storage medium storing instructions readable and executable by an electronic processor to perform a method for estimating singles rates for detectors of a detector array of a positron emission tomography (PET) imaging device, the method comprising:
    obtaining measured delayed coincidence rates for lines of response (LORs) defined by pairs of the detectors of the detector array; and
    generating estimated singles rates for the detectors of the detector array by an iterative optimization in which each iteration performs an update of estimates of the singles rates for the detectors by operations including:
        forward projecting the estimates of the singles rates for the detectors to generate estimates of delayed coincidence rates for the LORs;
        generating quantitative comparisons between the measured delayed coincidence rates for the LORs and the generated estimates of the delayed coincidence rates for the LORs;
        backprojecting the quantitative comparisons to generate corrections for the singles rates for the detectors;
        updating the estimates of the singles rates for the detectors using the generated corrections, wherein the estimated singles rates for the detectors of the detectors array comprise the estimates of the singles rates for output of the detectors by the iterative optimization when the iterative optimization satisfies a stopping criterion; and
    generating low-noise values for random coincidences rates from the updated estimates of the singles rates.

2. The non-transitory storage medium of claim 1 wherein the forward projecting comprises $s_i s_j$, for a LOR between detectors i and j where $s_i$ is the estimate of the singles rate for detector i and $s_j$ is the estimate of the singles rate for detector j.

3. The non-transitory storage medium of claim 2 wherein the quantitative comparison for the LOR between detectors i and j comprises the ratio $$\frac{R_{ij}}{2T\tau s_i s_j}, \text{ or } \frac{R_{ij}}{s'^{(n)}_i s'^{(n)}_j},$$

where $R_{ij}$ is the measured delayed coincidence rate for the LOR between detectors i and j.

4. The non-transitory storage medium of claim 1, wherein the quantitative comparisons are ratios of the measured delayed coincidence rates and the generated estimates of the delayed coincidence rates for the LORs.

5. The non-transitory storage medium of claim 1, wherein the updating includes normalizing the corrections.

6. The non-transitory storage medium of claim 1, wherein the updating includes adjusting the corrections by a relaxation term $(1-\lambda)+\lambda c$ where c is the correction and $\lambda$ is a relaxation factor.

7. The non-transitory storage medium of claim 1, wherein the iterative optimization is one of a maximum-likelihood-expectation maximization (ML-EM), a least square minimization, and an ordered subset expectation maximization (OSEM).

8. The non-transitory storage medium of claim 1, wherein the update of the estimate of the singles rate for the detector i comprises computing a value equal to:

$$s_i'^{(n+1)} = s_i'^{(n)} \left\{ (1-\lambda) + \lambda \frac{\sum_{j \in \{j_i\}} s_j'^{(n)} \frac{R_{ij}}{s_i'^{(n)} s_j'^{(n)}}}{\sum_{j \in \{j_i\}} s_j'^{(n)}} \right\},$$

for all valid $i$ wherein $s'_j$ is the estimate of the singles rate for detector i; $\{j_i\}$ is the set of detectors j that can form a valid LOR with the detector i; $R_{ij}$ is the measured delayed coincidence rate for the LOR between detectors i and j; $s'_j$ is the estimate of an effective singles rate for the other detectors j; and A is a relaxation factor between 0 and 1.

9. The non-transitory storage medium of claim 1, wherein the update of the estimate of the singles rate for the detector i comprises computing a value equal to:

$$s_i'^{(n+1)} = s_i'^{(n)} \left\{ (1-\lambda) + \lambda \frac{\sum_{j \in \{j_i\}} \frac{R_{ij}}{s_i'^{(n)} s_j'^{(n)}}}{\sum_{j \in \{j_i\}} 1} \right\},$$

for all valid $i$ wherein $s'_j$ is the estimate of the singles rate for detector i; $\{j_i\}$ is the set of detectors j that can form a valid LOR with the detector i; $R_{ij}$ is the measured delayed coincidence rate for the LOR between detectors i and j; $s'_j$ is the estimate of the singles rate for the other detectors j; and A is a relaxation factor between 0 and 1.

10. The non-transitory storage medium of claim 1, wherein the update of the estimate of the singles rate for the detector i comprises computing a value equal to:

$$s_i'^{(n+1)} = s_i'^{(n)} \left\{ (1-\lambda) + \lambda \frac{\sum_{e \in \{e_i\}} s_{j_e}'^{(n)} \frac{R_{ij}}{s_i'^{(n)} s_{j_e}'^{(n)}}}{\sum_{j \in \{j_i\}} s_j'^{(n)}} \right\},$$

for all valid $i$ wherein $s'_i$ is the estimate of the singles rate for detector i; $\{e_i\}$ is list mode data of all events that are recorded at an LOR connecting to detector i; $j_e$ is the set of detectors j that can form a valid LOR with the detector i; $s'_{j_e}$ is the estimate of the singles rate for the other detectors j; and λ is a relaxation factor between 0 and 1.

11. The non-transitory storage medium of claim 1, wherein the method is iteratively performed until a stopping criterion is met, the stopping criterion being defined by:

$$Q = \sum_{i=1}^{M} \sum_{j \in \{j_i\}} (s_i'^{(n)} s_j'^{(n)} - R_{ij})^2$$

where Q is a quality index; M is a number of all detectors; $s'^{(n)}_i$ is an effective singles rate for a selected detector in an imaging data acquisition device; $s'^{(n)}_i$ is an effective singles rate all other detectors in the detector array; and $R_{ij}$ is a delayed coincidence count.

12. The non-transitory storage medium of claim 1, further storing instructions readable and executable by the electronic processor to generate the low-noise values for the random coincidences rates according to:

$$(R_{ij}) = s_i'^{(final)} s_j'^{(final)}$$

where $(R_{ij})$ represents an expected random count at an $LOR_{ij}$ between detectors i and j; $s'^{(final)}_i$ is an effective singles rate for a selected detector in an imaging data acquisition device; and $s'^{(final)}_j$ is an effective singles rate all other detectors in the imaging data acquisition device.

13. An imaging system, comprising:
a positron emission tomography (PET) imaging device including a detector array having detectors;
at least one electronic processor programmed to:
obtain measured delayed coincidence rates for lines of response (LORs) defined by pairs of the detectors of the detector array; and
generate estimated singles rates for the detectors of the detector array by an iterative optimization in which each iteration performs an update of estimates of the singles rates for the detectors, wherein the iterative optimization generates the estimated singles rates by operations comprising:
forward projecting the estimates of the singles rates for the detectors to generate estimates of delayed coincidence rates for the LORs;
generating quantitative comparisons between the measured delayed coincidence rates for the LORs and the generated estimates of the delayed coincidence rates for the LORs;
backprojecting the quantitative comparisons to generate corrections for the singles rates for the detectors; and
updating the estimates of the singles rates for the detectors using the generated corrections, wherein the generated estimated singles rates for the detectors of the detectors array comprise the estimates of the singles rates for output of the detectors by the iterative optimization when the iterative optimization satisfies a stopping criterion; and
generating low-noise values for random coincidences rates from the updated estimates of the singles rates.

14. The imaging system of claim 13, wherein the forward projecting comprises $s_i s_j$, for a LOR between detectors i and j where $s_i$ is the estimate of the singles rate for detector i and $s_j$ is the estimate of the singles rate for detector j.

15. The imaging system of claim 14, wherein the quantitative comparisons are ratios of the measured delayed coincidence rates and the generated estimates of the delayed coincidence rates for the LORs.

16. The imaging system of claim 13, wherein the update of the estimate of the singles rate for the detector i comprises computing a value based on at least an estimate of the singles rate for detector i; the set of detectors j that can form a valid LOR with the detector i; a measured delayed coincidence rate for the LOR between detectors i and j; an estimate of the singles rate for the other detectors j; and a relaxation factor between 0 and 1.

17. The imaging system of claim 13, wherein the update of the estimate of the singles rate for the detector i comprises computing a value based on at least an estimate of the singles rate for detector i; list mode data of all events that are recorded at an LOR connecting to detector i; the set of detectors j that can form a valid LOR with the detector i; an estimate of the singles rate for the other detectors j; and a relaxation factor between 0 and 1.

18. The imaging system of claim 13, wherein the at least one electronic processor is programmed to iteratively generate the estimated singles rates for the detectors of the detector array until a stopping criterion is met, the stopping criterion being defined at least a quality index; a number of all detectors in the detector array; an effective singles rate for a selected detector in an imaging data acquisition device; an effective singles rate of all other detectors in the detector array; and a delayed coincidence count.

19. The imaging system of claim 13, wherein the at least one electronic processor is programmed to generate low-noise values for the random coincidences rates according to an expected random count at an $LOR_{ij}$ between detectors i and j; an effective singles rate for a selected detector in an imaging data acquisition device; and an effective singles rate all other detectors in the imaging data acquisition device.

20. The imaging system of claim 13, wherein the iterative optimization includes one of a maximum-likelihood-expectation maximization (ML-EM), a least square minimization, and an ordered subset expectation maximization (OSEM).

21. An imaging system, comprising:
a positron emission tomography (PET) imaging device including a detector array having detectors;
at least one electronic processor programmed to:
obtain measured delayed coincidence rates for lines of response (LORs) defined by pairs of the detectors of the detector array; and
generate estimated singles rates for the detectors of the detector array by an iterative forward projection/backprojection algorithm in which each iteration performs an update of estimates of the singles rates for the detectors, wherein the iterative forward projection/backprojection algorithm performs an update of estimates of the singles rates for the detectors by operations comprising:
forward projecting the estimates of the singles rates for the detectors o generate estimates of delayed coincidence rates for the LORs:
generating quantitative comparisons between the measured delayed coincidence rates for the LORs and the generated estimates of the delayed coincidence rates for the LORs;
backprojecting the quantitative comparisons to generate corrections for the singles rates for the detectors; and
updating the estimates of the singles rates for the detectors using the generated corrections;
wherein the estimated singles rates for the detectors of the detectors array comprise the estimates of the singles rates for output of the detectors by the iterative optimization when the iterative optimization satisfies a stopping criterion; and
wherein the quantitative comparisons are ratios of the measured delayed coincidence rates and the generated estimates of the random coincidence rates for the LORs.

22. The imaging system of claim 21, wherein the update of the estimate of the singles rate for the detector i comprises computing a value based on at least one of:
an estimate of the singles rate for detector i; the set of detectors j that can form a valid LOR with the detector i; a measured delayed coincidence rate for the LOR between detectors i and j; an estimate of the singles rate for the other detectors j; and a relaxation factor between 0 and 1; and
an estimate of the singles rate for detector i; list mode data of all events that are recorded at an LOR connecting to detector i; the set of detectors j that can form a valid LOR with the detector i; an estimate of the singles rate for the other detectors j; and a relaxation factor between 0 and 1.

23. The imaging system of claim 21, wherein the at least one electronic processor is programmed to generate low-noise values for the random coincidences rates according to an expected random count at an $LOR_{ij}$ between detectors i and j; an effective singles rate for a selected detector in an imaging data acquisition device; and an effective singles rate all other detectors in the imaging data acquisition device.

* * * * *